(12) United States Patent
Chang et al.

(10) Patent No.: US 8,455,093 B2
(45) Date of Patent: Jun. 4, 2013

(54) REACTIVE SILICON DIOXIDE COMPOUND AND OPTICAL PROTECTIVE FILM CONTAINING THE SAME

(75) Inventors: Te-Yi Chang, Bade (TW); Ming-Tzung Wu, Yunlin County (TW); Chiunn-Wen Chen, Hsinchu (TW); Jia-Ming Liu, Hsinchu (TW); Kuo-Tung Huang, Hsinchu County (TW)

(73) Assignee: Industrial Technology Research Institute, Hsinchu County (TW)

( * ) Notice: Subject to any disclaimer, the term of this patent is extended or adjusted under 35 U.S.C. 154(b) by 411 days.

(21) Appl. No.: 12/778,116

(22) Filed: May 11, 2010

(65) Prior Publication Data

US 2011/0088592 A1 Apr. 21, 2011

(30) Foreign Application Priority Data

Oct. 16, 2009 (TW) ............................... 98135044 A (51) Int. Cl.
*B32B 5/16* (2006.01)
(52) U.S. Cl.
USPC ............ 428/331; 428/1.3; 524/140; 524/287; 524/306; 524/321; 525/474
(58) Field of Classification Search
None
See application file for complete search history.

(56) References Cited

U.S. PATENT DOCUMENTS

| | | | |
|---|---|---|---|
| 6,828,006 B2 | 12/2004 | Takada et al. | |
| 6,844,033 B2 | 1/2005 | Kobayashi et al. | |
| 2012/0121910 A1 * | 5/2012 | Colton et al. | 428/412 |

* cited by examiner

Primary Examiner — Marc Zimmer (74) *Attorney, Agent, or Firm* — Pai Patent Trademark Law Firm; Chao-Chang David Pai

(57) ABSTRACT

A reactive silicon dioxide compound, wherein the formula of the reactive silicon dioxide compound is shown as Formula (I):

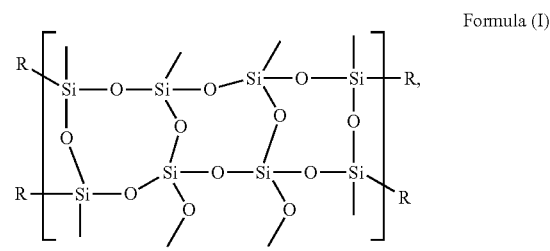

Formula (I)

where each R is a reactive group shown as Formula (II) or Formula (III), independently:

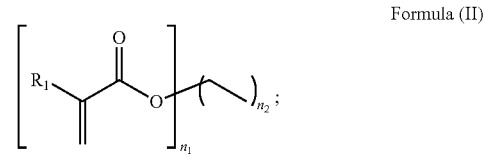

Formula (II)

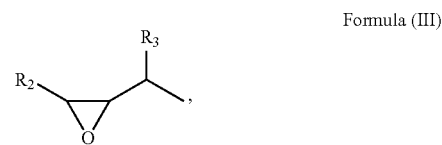

Formula (III)

and where $R_1$, $R_2$ and $R_3$ include H or $CH_3$, independently, $n_1$ is an integer of about 1-6 and $n_2$ is an integer of about 0-4. An optical protective film containing the reactive silicon dioxide compound is also provided.

10 Claims, 5 Drawing Sheets

REACTIVE SILICON DIOXIDE COMPOUND AND OPTICAL PROTECTIVE FILM CONTAINING THE SAME

CROSS REFERENCE TO RELATED APPLICATIONS

This Application claims priority of Taiwan Patent Application No. 098135044, filed on Oct. 16, 2009, the entirety of which is incorporated by reference herein.

BACKGROUND OF THE INVENTION

1. Field of the Invention

The present invention relates to a reactive silicon dioxide compound and an optical protective film, and in particular relates to an optical protective film containing a reactive silicon dioxide compound, wherein the reactive silicon dioxide compound may reduce phase difference and enhance transparency of the optical protective film.

2. Description of the Related Art

Nano-scaled silicon dioxide material is used in polymer material as a filler material to increase surface hardness, mechanical strength and heat tolerance of the polymer material. Such a polymer material is widely applied in coating material, film, and the surface treatment for automobiles.

At present, nano-scaled silicon dioxide material is applied in optical protective films. However, for optical protective films, the greater the amount of nano-scaled silicon dioxide material used, the greater the haze therein.

A. Tagaya, H. Ohkita, M. Mukaoh, R. Sakaguchi, Y. Koike, Science, 301, 812, (2003) discloses that a polymer material is added into an inorganic salt crystalline compound to reduce an $R_0$ value thereof. However, the $R_{th}$ value is not reduced.

U.S. Pat. No. 6,828,006 and U.S. Pat. No. 6,844,033 discloses that the maximum content of a nano-scaled silicon dioxide material used to making a triacetate cellulose triacetate cellulose film should be 0.3%, if more than 0.3% is used in a cellulose triacetate cellulose film, transparency and haze of an optical protective film would decrease and increase, respectively.

A novel optical protective film which has low phase difference and low haze is desired. Therefore, in the invention, an optical protective film containing a reactive nano-scaled silicon dioxide material which has low phase difference and low haze is provided. Briefly, due to surface modification of a reactive nano-scaled silicon dioxide material, the reactive nano-scaled silicon dioxide material may be more compatible with a polymer thereby increasing transparency and decreasing haze.

The reactive silicon dioxide compound of the invention may improve the out-of-plane problem of polarized light optical protective film, reduce light leakage at large view angles and color shift, and reduce contrast of bright state and dark state. Furthermore, the reactive silicon dioxide compound of the invention may be applied in plastic solar energy condenser lenses of the optical field.

BRIEF SUMMARY OF THE INVENTION

The invention provides a reactive silicon dioxide compound, wherein the formula of the reactive silicon dioxide compound is shown as Formula (I):

Formula (I)

where each R is a reactive group shown as Formula (II) or Formula (III), independently:

Formula (II)

Formula (III)

and where $R_1$, $R_2$ and $R_3$ comprise H or $CH_3$, independently, $n_1$ is an integer of about 1-6 and $n_2$ is an integer of about 0-4.

The invention further provides an optical protective film, comprising: the reactive silicon dioxide compound as mentioned above, wherein content of the reactive silicon dioxide compound is about 5-50 wt %; and a triacetate cellulose, wherein content of the r triacetate cellulose is about 50-95 wt %.

A detailed description is given in the following embodiments with reference to the accompanying drawings.

BRIEF DESCRIPTION OF THE DRAWINGS

The present invention can be more fully understood by reading of the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating of the general principles of the invention and should not be taken in a limiting sense. The scope of the invention is best determined by reference to the appended claims.

The invention provides a reactive silicon dioxide compound and an optical protective film containing the same. The optical protective film comprises the reactive silicon dioxide compound and triacetate cellulose. A formula of the reactive silicon dioxide compound is shown as Formula (I):

Formula (I)

wherein each R may be a reactive group shown as Formula (II) or Formula (III), independently:

Formula (II)

Formula (III)

and wherein $R_1$, $R_2$ and $R_3$ may comprise H or $CH_3$, independently, $n_1$ may be an integer of about 1-6 and $n_2$ may be an integer of about 0-4. In one embodiment, the optical protective film comprises the reactive silicon dioxide compound with a content of 5-50 wt % and a triacetate cellulose with a content of 50-95 wt %. Using of the previously mentioned content ranges of the reactive silicon dioxide compound of the invention, phase difference, transparency and haze for an optical protective film may be respectively reduced, increased and decreased when compared to an optical protective film formed by the conventional methods.

Figure 1A:
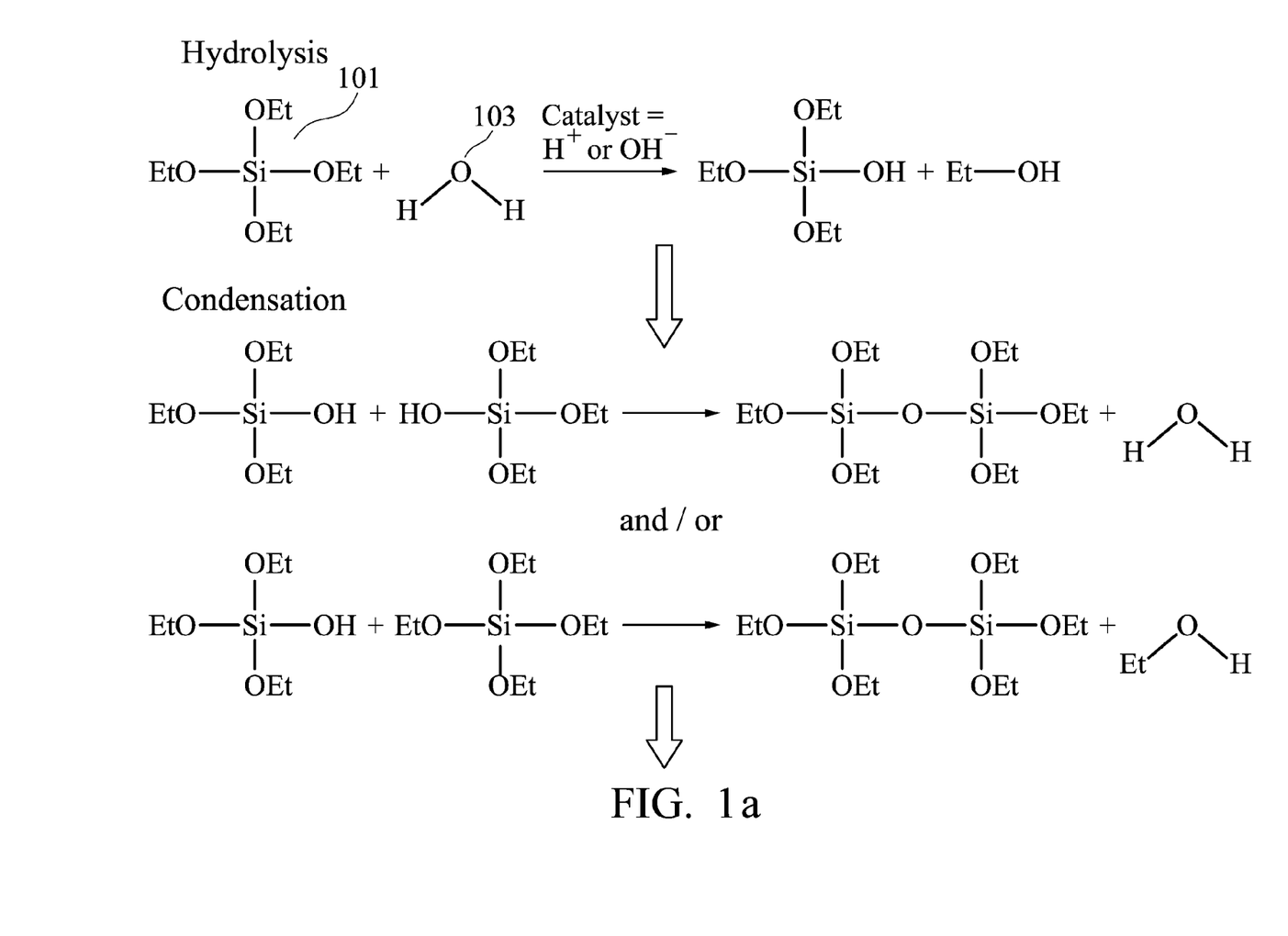
FIG. 1a and FIG. 1b show a detailed mechanism for forming a reactive silicon dioxide compound.
Figure 1B:
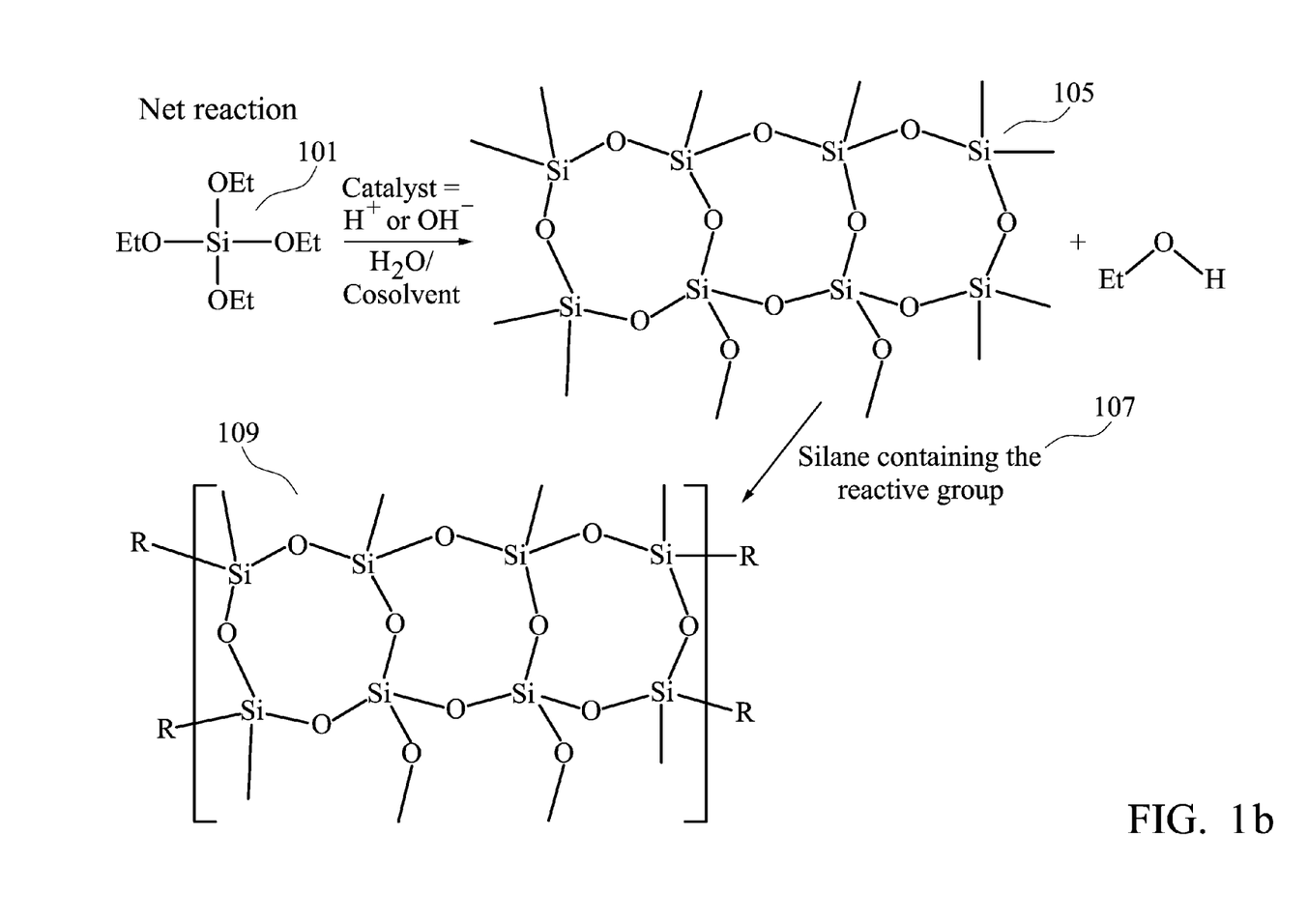

The reactive group in the reactive silicon dioxide compound may have a content of about 0.1-95 wt %. The reactive silicon dioxide is formed by reacting a silicon dioxide with a silane containing the reactive group mentioned above. The detailed mechanism for forming a reactive silicon dioxide compound is shown in FIG. 1a and FIG. 1b. Referring of to FIG. 1a, first, tetraethoxy silane (TEOS) 101 is added to water 103 for the hydrolysis and condensation and a silicon dioxide inorganic sol gel 105 is formed. The net reaction of the hydrolysis and condensation is shown in the upper part of FIG. 1b. Then, the silicon dioxide inorganic sol gel 105 is allowed to react with a silane containing the reactive group 107 to produce the reactive silicon dioxide compound 109 of the invention, as shown in FIG. 1b. Furthermore, the reaction time and reaction temperature for silicon dioxide reacting with the silane containing the reactive group are about 10-600 minutes and about 10-100° C., respectively and in one embodiment the reaction temperature is about 40° C. The silane containing the reactive group may comprise, but is not limited to 3-(trimethoxysilyl)-propyl methacrylate or 3-glycidoxypropyl trimethoxysilane, etc., or combinations thereof. A range of the size of the particles of the reactive silicon dioxide compound is about 0.1-100 nm.

In addition, content of an acetyl group in the triacetate cellulose is about 34-44 wt %.

The optical protective film may further comprise a plasticizer. Content of the plasticizer may be about 4-20 wt %. The plasticizer may comprise triphenyl phosphate, 2-biphenylyl diphenyl phosphate or ethyl phthalyl ethyl glycolate, etc.

Figure 2:
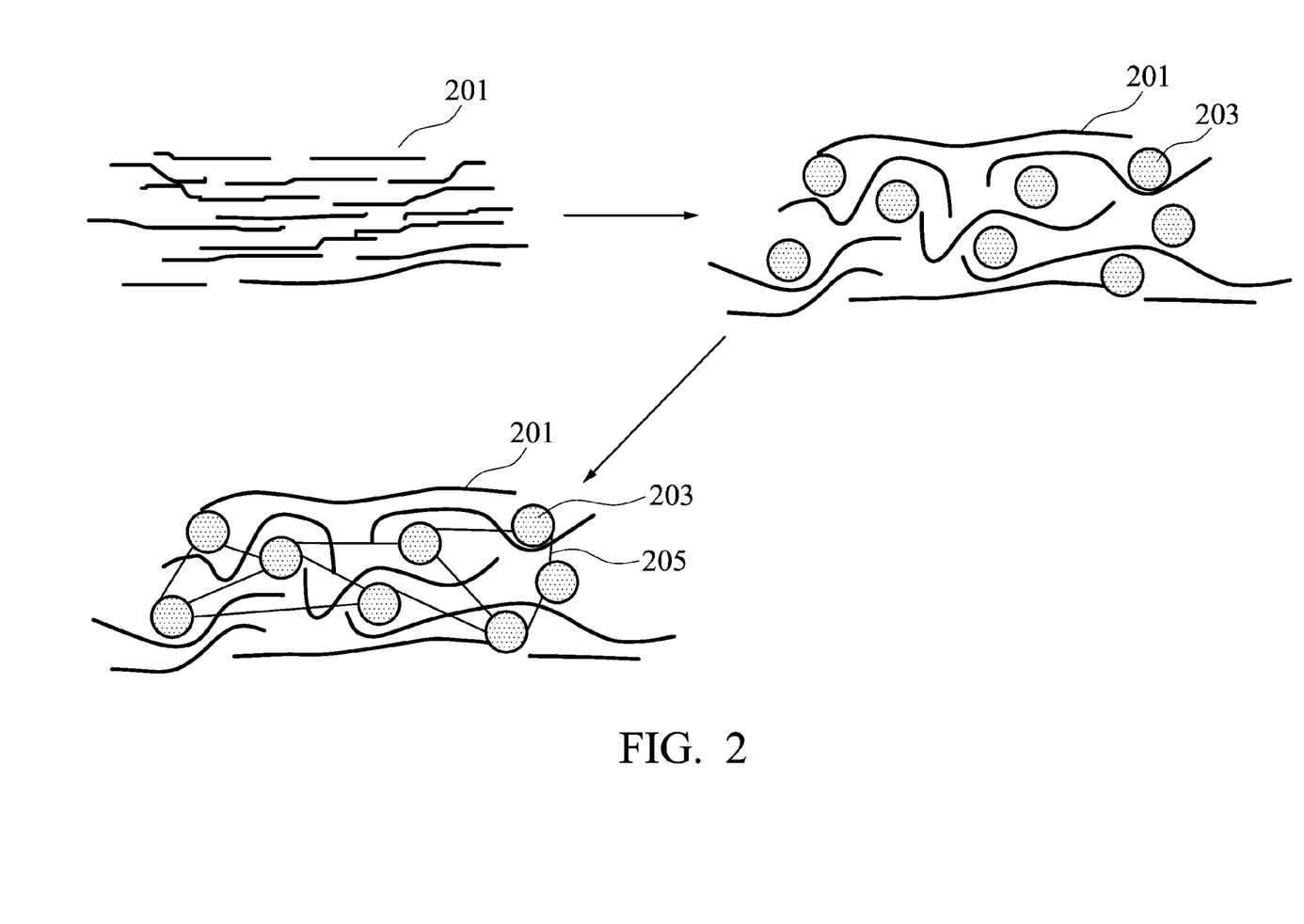
FIG. 2 is a schematic view showing a reactive silicon dioxide compound being introduced into polymer.

Introduction of the reactive silicon dioxide 203 into the polymer 201 will interfere with the in plane arrange of the polymer in the film and result in crosslink 205 to stabilize the structure of the polymer (see FIG. 2). Accordingly, when compared to a traditional optical protective film, the optical protective film of the invention has lower phase difference values, $R_0$ and $R_{th}$. Meanwhile, $R_0=(N_X-N_Y) \times d$, $N_X$ and $N_Y$ are main refractive indices on the optical protective film, d is the thickness of the optical protective film and the range of the test wavelength of light is 400-700 nm. Also, $R_{th}=((N_X+N_Y)/2-N_Z) \times d$, $N_Z$ is the main refractive index in the direction of thickness of the optical protective film, d is the thickness of the optical protective film and the range of the test weave length of light is 400-700 nm. The $R_0$ value of the optical protective film mentioned above is about 0-3 nm and the $R_{th}$ value of the optical protective film mentioned above is about 0-100 nm. Haze of the optical protective film is about 0.1-2.0. Thickness of the optical protective film is about 1-500 μm.

EXAMPLE

1. Synthesis of the Reactive Silicon Dioxide Compound

Example A 50 ml of 20 wt % $SiO_2$ dispersion (in $CH_2Cl_2$; average particle size: 30±6 nm) (nano sol, product of Chang Chun Plastics Co., LTD, Taiwan) and 15 ml of 3-(trimethoxysilyl)-propyl methacrylate were mixed for reaction at 40° C. for 4 hours, and then cooled to room temperature and continuously stirred for 48 hours. After that, an $SiO_2$ dispersion containing a reactive group of methacrylate was obtained (average particle size: 10±5 nm).

Example B 50 ml of 20 wt % $SiO_2$ dispersion (in $CH_2Cl_2$; average particle size: 30±6 nm) (nano sol, product of Chang Chun Plastics Co., LTD, Taiwan) and 15 ml of 3-glycidoxypropyl trimethoxysilane were mixed for reaction at 40° C. for 4 hours, and then cooled to room temperature and continuously stirred for 48 hours. After that, an $SiO_2$ dispersion containing a reactive group of glycidoxyl was obtained (average particle size: 17±5 nm).

Example C 50 ml of 20 wt % $SiO_2$ dispersion (in $CH_2Cl_2$; average particle size: 30±6 nm) (nano sol, product of Chang Chun Plastics Co., LTD, Taiwan) and 15 ml of 3-(trimethoxysilyl)-propyl methacrylate were mixed for reaction at 40° C. for 4 hours, next 15 ml of 3-glycidoxypropyl trimethoxysilane were added for reaction at 40° C. for 4 hours, and then cooled to room temperature and continuously stirred for 48 hours. After that, an $SiO_2$ dispersion containing reactive groups of methacrylate and glycidoxyl were obtained (average particle size: 15±6 nm).

2. Determination of the Content of the Reactive Group in the Reactive Silicon Dioxide Compound $SiO_2$ dispersions containing a reactive group obtained from Examples A-C, respectively, were placed in an oven with a temperature of 105° C. for drying for 3 hours, and then the dried $SiO_2$ samples were placed into a dry box for the surrounding of temperature to return to room temperature for 6 hours. Next, the $SiO_2$ samples were placed in a thermogravimetric analyzer (TGA) under an atmosphere of nitrogen and the temperature was raised so that the reactive group in the respective $SiO_2$ samples was cleaved and weight of the respective $SiO_2$ samples decreased. Weight changes of the respective $SiO_2$ samples with temperature or time were recorded to determine the content ratio of the reactive group in the respective $SiO_2$ samples. The results are shown in Table 1.

TABLE 1

The content of the reactive group in the $SiO_2$ material

| TGA heat cleavage temperature and content % | Example A | Example B | Example C |
|---|---|---|---|
| 25~100° C. (%) | 0.33 | 0.21 | 0.29 |
| 100~400° C. (%) | 31.25 | 32.15 | 31.80 |
| 400~600° C. (%) | 68.42 | 67.64 | 67.91 |
| Cleavage temperature ° C. | 286.30 | 292.05 | 290.70 |
| Content ratio of the reactive group (%) | 31.35 | 32.21 | 31.89 |

3. Formation of the Low Phase Difference Optical Protective Film (1) Addition of the Reactive Silicon Dioxide Compound Synthesize in Example A Example A-1

Preparation of a Triacetate Cellulose (TAC) Dope 35.54 g of triacetate cellulose, 3.95 g of triphenyl phosphate and 224.64 g of a $CH_2Cl_2$/MeOH mixed solution (volume ratio: $CH_2Cl_2$/MeOH=95/5) were added into a 500 ml bottle. The bottle was rolled at a speed of 15 rounds/minute at room temperature for 24 hours, continuously. After that, 10.5 g of the reactive silicon dioxide compound dispersion (20 wt %) synthesized in Example A was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The completed triacetate cellulose (TAC) dope was poured into a mold. The interval between the mold and a glass plate was controlled at 700 μm. The triacetate cellulose (TAC) dope was applied on a glass plate at a linear speed of 2.5 cm/second by the mold. After the application was completed, the glass plate with a wet film was placed in an oven at 100° C. for drying, for 8 hours. Next, the dried film was peeled from the glass plate and placed in a box of RH50, with a constant temperature of 25° C. for saturation for 8 hours to obtain an optical protective film with an average thickness of 71±2 μm.

Determination of $R_0$ and $R_{th}$:

The obtained optical protective film was placed in an AXOMETRIX spectrometer to analyze the obtained optical protective film. The range of wavelength of light for analyzing $R_0$ and $R_{th}$ values of the optical protective film was 400-700 nm. The determined $R_0$ value was 0.16 nm and the determined $R_{th}$ value was 75 nm.

Determination of Haze

The obtained optical protective film was placed in a haze meter to analyze the obtained optical protective film. The range of wavelength of light for analyzing of the haze value of the optical protective film was 400-700 nm. The determined haze value was 0.85.

Example A-2

Preparation of a Triacetate Cellulose (TAC) Dope 33.65 g of triacetate cellulose, 3.74 g of triphenyl phosphate and 217.08 g of a $CH_2Cl_2$/MeOH mixed solution (volume ratio $CH_2Cl_2$/MeOH=95/5) were added into a 500 ml bottle. The bottle was rolled at a speed of 15 rounds/minute at room temperature for 24 hours, continuously. After that, 21 g of the reactive silicon dioxide compound dispersion (20 wt %) synthesized in Example A was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The method the same as that mentioned in Example A-1 was used. An optical protective film with an average thickness of 78±2 μm was obtained.

Determination of $R_0$ and $R_{th}$:

The method the same as that mentioned in Example A-1 was used. The determined $R_0$ value was 0.17 nm and the determined $R_{th}$ value was 71 nm.

Determination of Haze

The method the same as that mentioned in Example A-1 was used. The determined haze value was 1.42.

Example A-3

Preparation of a Triacetate Cellulose (TAC) Dope 31.76 g of triacetate cellulose, 3.53 g of triphenyl phosphate and 209.52 g of a $CH_2Cl_2$/MeOH mixed solution (volume ratio $CH_2Cl_2$/MeOH=95/5) were added into a 500 ml bottle. The bottle was rolled at a speed of 15 rounds/minute at room temperature for 24 hours, continuously. After that, 31.50 g of the reactive silicon dioxide compound dispersion (20 wt %) synthesized in Example A was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The method the same as that mentioned in Example A-1 was used. An optical protective film with an average thickness of 80±2 μm was obtained.

Determination of $R_0$ and $R_{th}$:

The method the same as that mentioned in Example A-1 was used. The determined $R_0$ value was 0.18 nm and the determined $R_{th}$ value was 57 nm.

Determination of Haze

The method the same as that mentioned in Example A-1 was used. The determined haze value was 2.0.

Example A-4

Preparation of a Triacetate Cellulose (TAC) Dope 26.09 g of triacetate cellulose, 2.90 g of triphenyl phosphate and 186.84 g of a $CH_2Cl_2$/MeOH mixed solution (volume ratio CH$_2$Cl$_2$/MeOH=95/5) were added into a 500 ml bottle. The bottle was rolled at a speed of 15 rounds/minute at room temperature for 24 hours, continuously. After that, 63 g of the reactive silicon dioxide compound dispersion (20 wt %) synthesized in Example A was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The method the same as that mentioned in Example A-1 was used. An optical protective film with an average thickness of 90±2 μm was obtained.

Determination of R$_0$ and R$_{th}$:

The method the same as that mentioned in Example A-1 was used. The determined R$_0$ value was 0.17 nm and the determined R$_{th}$ value was 25 nm.

Determination of Haze

The method the same as that mentioned in Example A-1 was used. The determined haze value was 0.8.

Example A-5

Preparation of a Triacetate Cellulose (TAC) Dope 16.47 g of triacetate cellulose, 4.12 g of triphenyl phosphate and 156.60 g of a CH$_2$Cl$_2$/MeOH mixed solution (volume ratio CH$_2$Cl$_2$/MeOH=95/5) were added into a 500 ml bottle. The bottle was rolled at a speed of 15 rounds/minute at room temperature for 24 hours, continuously. After that, 105 g of the reactive silicon dioxide compound dispersion (20 wt %) synthesized in Example A was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The method the same as that mentioned in Example A-1 was used. An optical protective film with an average thickness of 100±2 μm was obtained.

Determination of R$_0$ and R$_{th}$:

The method the same as that mentioned in Example A-1 was used. The determined R$_0$ value was 0.15 nm and the determined R$_{th}$ value was 1 nm.

Determination of Haze

The method the same as that mentioned in Example A-1 was used. The determined haze value was 1.0.

The content ratios of the reactive silicon dioxide compound to the triacetate cellulose in Examples A-1 to A-5 and the R$_0$ and R$_{th}$ values of the film therefrom are shown in Table 2.

TABLE 2

The content ratios of the reactive silicon dioxide compound to the triacetate cellulose in Examples A-1 to A-5 and the R$_0$ and R$_{th}$ values of the optical protective films

| | Reactive silicon dioxide compound synthesized in Example A (%) | Triacetate cellulose (TCA) (%) | R$_0$ (nm) | R$_{th}$ (nm) |
|---|---|---|---|---|
| Example A-1 | 5% | 95% | less than 0.3 | 75 |
| Example A-2 | 10% | 90% | less than 0.3 | 71 |
| Example A-3 | 15% | 85% | less than 0.3 | 57 |
| Example A-4 | 30% | 70% | less than 0.3 | 25 |
| Example A-5 | 50% | 50% | less than 0.3 | 1 |

Figure 3A:
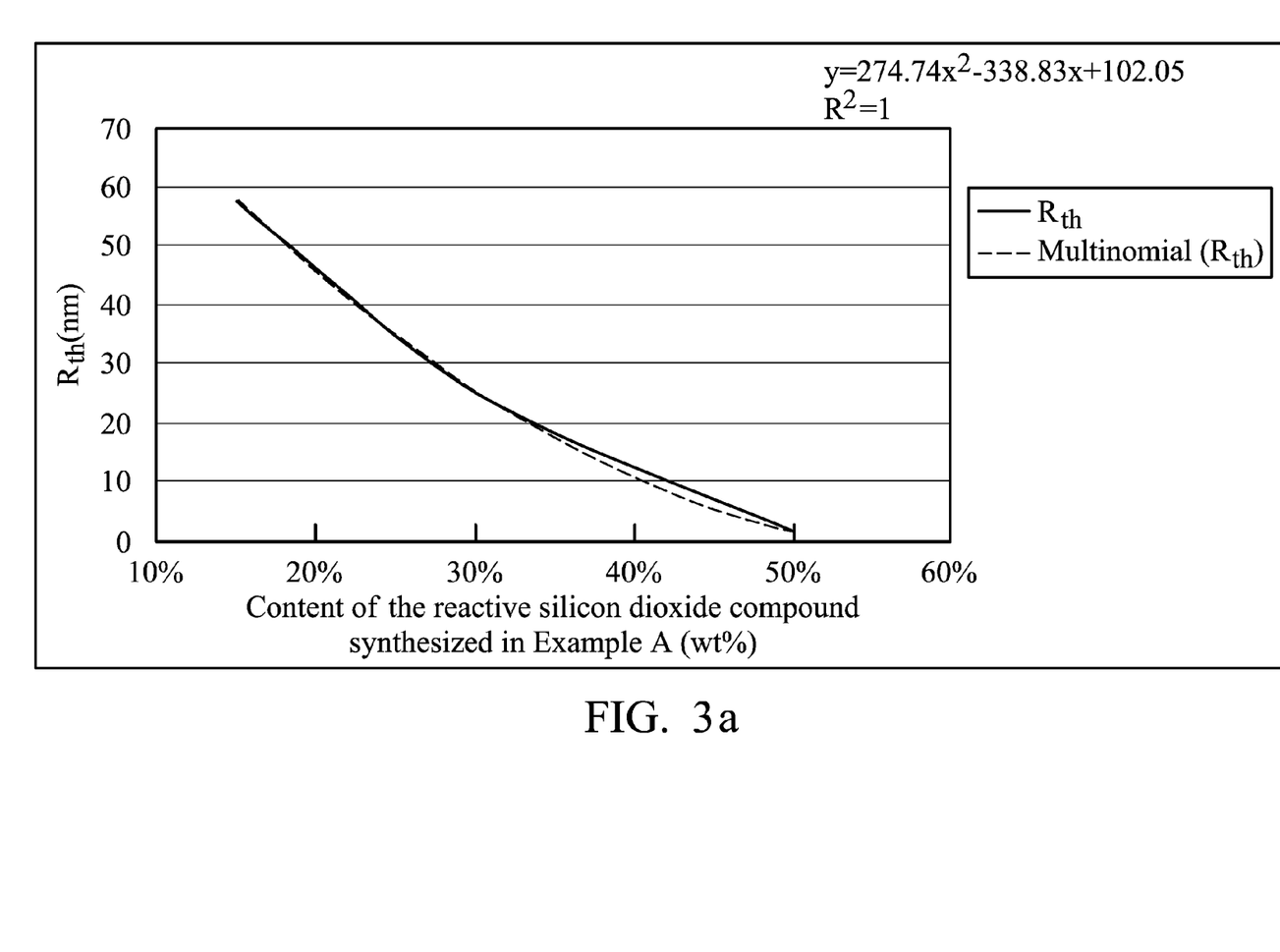
FIG. 3a shows the relationship between the content of the reactive silicon dioxide compound synthesized in Example A and $R_{th}$ value of the optical protective film.

The relationship between the content of the reactive silicon dioxide compound synthesized in Example A and R$_{th}$ value of the optical protective film is shown in FIG. 3a. According to FIG. 3a, it is understood that when the content of the reactive silicon dioxide compound synthesized in Example A increases, the R$_{th}$ value of the optical protective film is decreases.

(2) Addition of the Reactive Silicon Dioxide Compound Synthesized in Example B

Example B-1

Preparation of a Triacetate Cellulose (TAC) Dope 33.65 g of triacetate cellulose, 3.74 g of triphenyl phosphate and 217.08 g of a CH$_2$Cl$_2$/MeOH mixed solution (volume ratio CH$_2$Cl$_2$/MeOH=95/5) were added into a 500 ml bottle. The bottle was rolled at a speed of 15 rounds/minute at room temperature for 24 hours, continuously. After that, 21 g of the reactive silicon dioxide compound dispersion (20 wt %) synthesize in Example B was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The completed triacetate cellulose (TAC) dope was poured into a mold. The interval between the mold and a glass plate was controlled at 700 μm. The triacetate cellulose (TAC) dope was applied on the glass plate at a linear speed of 2.5 cm/second by the mold. After application was completed, the glass plate with a wet film was placed in an oven at 100° C. for drying, for 8 hours. Next, the dried film was peeled from the glass plate and placed in a box of RH50, with a constant temperature of 25° C. for saturation for 8 hours to obtain an optical protective film with an average thickness of 93±2 μm.

Determination of R$_0$ and R$_{th}$:

The obtained optical protective film was placed in an AXOMETRIX spectrometer to analyze the obtained optical protective film. The range of wavelength of light for analyzing R$_0$ and R$_{th}$ values of the optical protective film was 400-700 nm. The determined R$_0$ value was 0.13 nm and the determined R$_{th}$ value was 52 nm.

Determination of Haze

The obtained optical protective film was placed in a haze meter to analyze the obtained optical protective film. The range of wavelength of light for analyzing haze value of the optical protective film was 400-700 nm. The determined haze value was 0.48.

Example B-2

Preparation of a Triacetate Cellulose (TAC) Dope 29.87 g of triacetate cellulose, 3.32 g of triphenyl phosphate and 201.96 g of a CH$_2$Cl$_2$/MeOH mixed solution (volume ratio $CH_2Cl_2$/MeOH=95/5) were added into a 500 ml bottle. The bottle was rolled at a speed of 15 rounds/minute at room temperature for 24 hours, continuously. After that, 42 g of the reactive silicon dioxide compound dispersion (20 wt %) synthesized in Example B was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The method the same as that mentioned in Example B-1 was used. An optical protective film with an average thickness of 79±2 μm was obtained.

Determination of $R_0$ and $R_{th}$:

The method the same as that mentioned in Example B-1 was used. The determined $R_0$ value was 0.29 nm and the determined $R_{th}$ value was 27 nm.

Determination of Haze

The method the same as that mentioned in Example B-1 was used. The determined haze value was 0.37.

Example B-3

Preparation of a Triacetate Cellulose (TAC) Dope 26.09 g of triacetate cellulose, 2.90 g of triphenyl phosphate and 186.84 g of a $CH_2Cl_2$/MeOH mixed solution (volume ratio $CH_2Cl_2$/MeOH=95/5) were added into a 500 ml bottle. The bottle was rolled at a speed of 15 rounds/minute at room temperature for 24 hours, continuously. After that, 63 g of the reactive silicon dioxide compound dispersion (20 wt %) synthesized in Example B was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The method the same as that mentioned in Example B-1 was used. An optical protective film with an average thickness of 75±2 μm was obtained.

Determination of $R_0$ and $R_{th}$:

The method the same as that mentioned in Example B-1 was used. The determined $R_0$ value was 0.12 nm and the determined $R_{th}$ value was 12 nm.

Determination of Haze

The method the same as that mentioned in Example B-1 was used. The determined haze value was 1.06.

Example B-4

Preparation of a Triacetate Cellulose (TAC) Dope 22.31 g of triacetate cellulose, 2.48 g of triphenyl phosphate and 171.72 g of a $CH_2Cl_2$/MeOH mixed solution (volume ratio $CH_2Cl_2$/MeOH=95/5) were added into a 500 ml bottle. The bottle was rolled at a speed of 15 rounds/minute at room temperature for 24 hours, continuously. After that, 84 g of the reactive silicon dioxide compound dispersion (20 wt %) synthesized in Example B was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The method the same as that mentioned in Example B-1 was used. An optical protective film with an average thickness of 95±2 μm was obtained.

Determination of $R_0$ and $R_{th}$:

The method the same as that mentioned in Example B-1 was used. The determined $R_0$ value was 0.27 nm and the determined $R_{th}$ value was 2.5 nm.

Determination of Haze

The method the same as that mentioned in Example B-1 was used. The determined haze value was 0.23.

Example B-5

Preparation of a Triacetate Cellulose (TAC) Dope 18.53 g of triacetate cellulose, 2.06 g of triphenyl phosphate and 105 g of a $CH_2Cl_2$/MeOH mixed solution (volume ratio $CH_2Cl_2$/MeOH=95/5) were added into a 500 ml bottle. The bottle was rolled at a speed of 15 rounds/minute at room temperature for 24 hours, continuously. After that, 156.60 g of the reactive silicon dioxide compound dispersion (20 wt %) synthesized in Example B was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The method the same as that mentioned in Example B-1 was used. An optical protective film with an average thickness of 83±2 μm was obtained.

Determination of $R_0$ and $R_{th}$:

The method the same as that mentioned in Example B-1 was used. The determined $R_0$ value was 0.08 nm and the determined $R_{th}$ value was 1.9 nm.

Determination of Haze

The method the same as that mentioned in Example B-1 was used. The determined haze value was 1.12.

The content ratios of the reactive silicon dioxide compound to the triacetate cellulose in Examples B-1 to B-5 and the $R_0$ and $R_{th}$ values of the film therefrom are shown in Table 3.

TABLE 3

The content ratios of the reactive silicon dioxide compound to the triacetate cellulose in Examples B-1 to B-5 and the $R_0$ and $R_{th}$ values of the optical protective films

| | Reactive silicon dioxide compound synthesized in Example B (%) | Triacetate cellulose (TCA) (%) | $R_0$ (nm) | $R_{th}$ (nm) |
|---|---|---|---|---|
| Example B-1 | 5% | 95% | less than 0.3 | 52 |
| Example B-2 | 10% | 90% | less than 0.3 | 28 |
| Example B-3 | 15% | 85% | less than 0.3 | 12 |
| Example B-4 | 30% | 70% | less than 0.3 | 2.5 |
| Example B-5 | 50% | 50% | less than 0.3 | 1.9 |

Figure 3B:
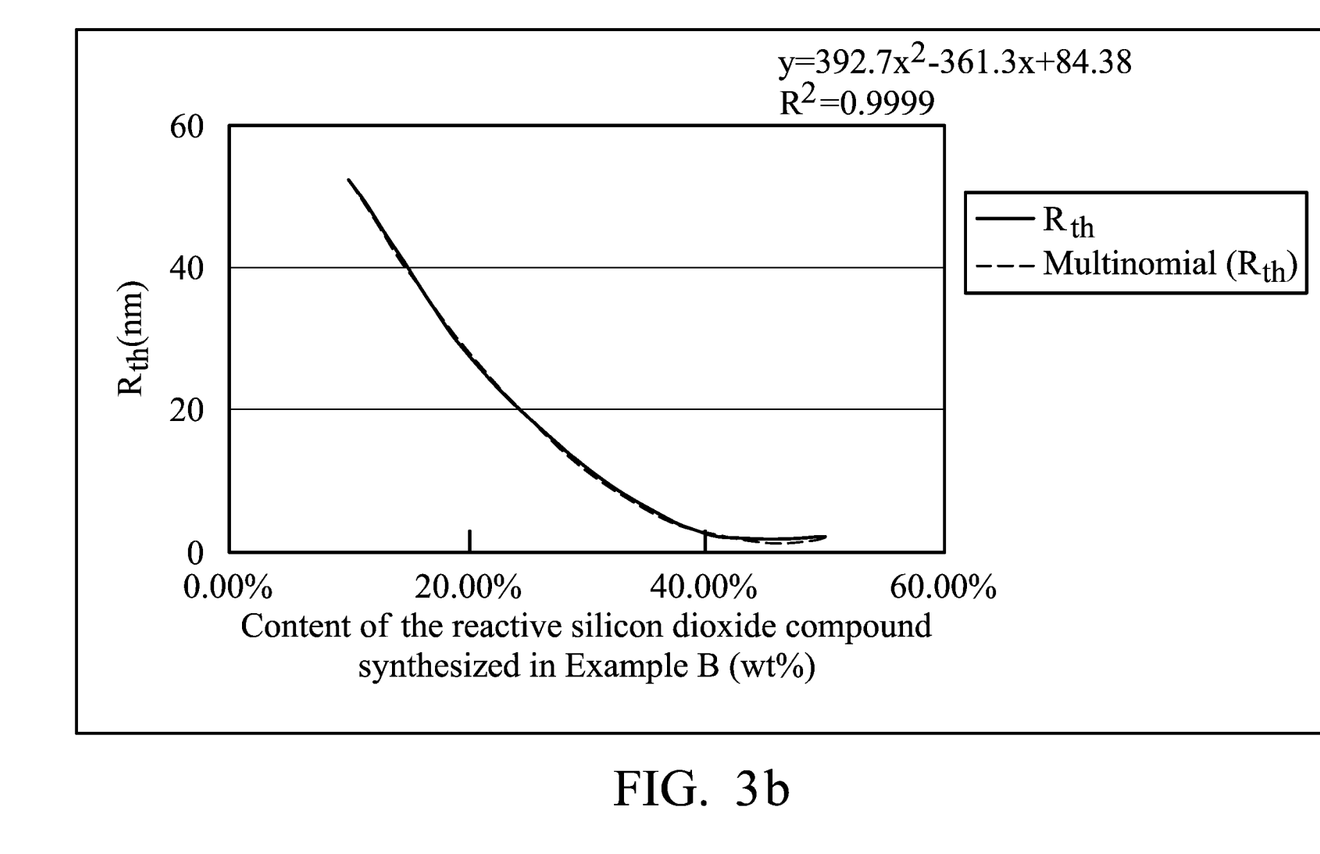
FIG. 3b shows the relationship between the content of the reactive silicon dioxide compound synthesized in Example B and $R_{th}$ value of the optical protective film.

The relationship between the content of the reactive silicon dioxide compound synthesized in Example B and $R_{th}$ value of the optical protective film is shown in FIG. 3b. According to FIG. 3b, it is understood that when the content of the reactive silicon dioxide compound synthesized in Example B increases, the $R_{th}$ value of the optical protective film is decreases.

(3) Comparative Examples

Addition of a Non-Modified Silicon Dioxide Compound

Comparative Example 1

Preparation of a Triacetate Cellulose (TAC) Dope 31.76 g of triacetate cellulose, 3.53 g of triphenyl phosphate and 209.52 g of a $CH_2Cl_2$/MeOH mixed solution (volume ratio $CH_2Cl_2$/MeOH=95/5) were added into a 500 ml bottle. The bottle was rolled at a speed of 15 rounds/minute at room temperature for 24 hours, continuously. After that, 31.50 g 20 wt % silicon dioxide compound dispersion (in $CH_2Cl_2$; average particle size: 30±6 nm) (nano sol, product of Chang Chun Plastics Co., LTD, Taiwan) was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The triacetate cellulose (TAC) dope prepared completely mentioned above was poured into a mold. The interval between the mold and a glass plate was controlled at 700 μm. The triacetate cellulose (TAC) dope was applied on the glass plate at a linear speed of 2.5 cm/second by the mold. After application was completed, the glass plate with a wet film was placed in an oven at 100° C. for drying, for 8 hours. Next, the dried film was peeled from the glass plate and placed in a box of RH50, with a constant temperature of 25° C. for saturation for 8 hours to obtain an optical protective film with an average thickness of 80±2 μm.

Determination of Haze

The obtained optical protective film was placed in a haze meter to analyze the obtained optical protective film. The range of wavelength of light for analyzing haze value of the optical protective film was 400-700 nm. The determined haze value was 7.0.

Comparative Example 2

Preparation of a Triacetate Cellulose (TAC) Dope 26.09 g of triacetate cellulose, 2.90 g of triphenyl phosphate and 186.84 g of a $CH_2Cl_2$/MeOH mixed solution (volume ratio $CH_2Cl_2$/MeOH=95/5) were added into a 500 ml bottle. The bottle was rolled at a speed of 15 rounds/minute at room temperature for 24 hours, continuously. After that, 63 g 20 wt % silicon dioxide compound dispersion (in $CH_2Cl_2$; average particle size: 30±6 nm) (nano sol, product of Chang Chun Plastics Co., LTD, Taiwan) was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The method the same as that mentioned in Comparative example 1 was used. An optical protective film with an average thickness of 90±2 μm was obtained.

Determination of Haze

The method the same as that mentioned in Comparative example 1 was used. The determined haze value was 10.

Comparative Example 3

Preparation of a Triacetate Cellulose (TAC) Dope 16.47 g of triacetate cellulose, 4.12 g of triphenyl phosphate and 156.60 g of a $CH_2Cl_2$/MeOH mixed solution (volume ratio $CH_2Cl_2$/MeOH=95/5) were added into a 500 ml bottle. The bottle was rolled at a speed of 15 rounds/minute at room temperature for 24 hours, continuously. After that, 105 g 20 wt % silicon dioxide compound dispersion (in $CH_2Cl_2$; average particle size: 30±6 nm) (nano sol, product of Chang Chun Plastics Co., LTD, Taiwan) was added into the 500 ml bottle and the bottle was rolled at room temperature for 24 hours. Next, the mixture in the bottle was filtered with a filter film made of 15 μm polypropylene (PP) to obtain a transparent triacetate cellulose dope.

Preparation of an Optical Protective Film

The method the same as that mentioned in Comparative example 1 was used. An optical protective film with an average thickness of 100±2 μm was obtained.

Determination of Haze

The method the same as that mentioned in Comparative example 1 was used. The determined haze value was 14.

Haze of the optical protective films of Examples A-1 to A-5 and the optical protective films of Comparative examples 1 to 3 are shown in Table 4.

TABLE 4

Haze of the optical protective films of Examples A-3 to A-5 and the optical protective films of Comparative examples 1 to 3

| Content of silicon dioxide compound (%) | Haze of the optical protective films of Examples (containing the reactive silicon dioxide compound of Example A) | Haze of the optical protective films of Comparative examples (containing the non-modified silicon dioxide compound) |
|---|---|---|
| 15% | 2.0 (Example A-3) | 7.0 (Comparative example 1) |
| 30% | 0.8 (Example A-4) | 10 (Comparative example 2) |
| 50% | 1.0 (Example A-5) | 14 (Comparative example 3) |

Table 4 shows that under the condition where the content of a silicon dioxide compound is the same, the optical protective films containing the reactive silicon dioxide compound of the invention have lower haze when compared to the optical protective films containing a non-modified silicon dioxide compound.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An optical protective film, comprising:
a reactive silicon dioxide compound, wherein the formula of the reactive silicon dioxide compound is shown as Formula (I):

Formula (I)

wherein each R is a reactive group shown as Formula (II) or Formula (III), independently:

Formula (II)

Formula (III)

wherein $R_1$, $R_2$ and $R_3$ comprise H or $CH_3$, independently, $n_1$ is an integer of about 1-6 and $n_2$ is an integer of about 0-4, and wherein content of the reactive silicon dioxide compound is about 5-50 wt %; and a triacetate cellulose, wherein content of the r triacetate cellulose is about 50-95 wt %.

2. The optical protective film as claimed in claim 1, wherein a range of the size of the particles of the reactive silicon dioxide compound is about 0.1-100 nm.

3. The optical protective film as claimed in claim 1, wherein content of an acetyl group in the triacetate cellulose is about 34-44 wt %.

4. The optical protective film as claimed in claim 1, further comprising a plasticizer.

5. The optical protective film as claimed in claim 4, wherein content of the plasticizer is about 4-20 wt %.

6. The optical protective film as claimed in claim 4, wherein the plasticizer comprises triphenyl phosphate, 2-biphenylyl diphenyl phosphate or ethyl phthalyl ethyl glycolate.

7. The optical protective film as claimed in claim 1, wherein an $R_0$ value of the optical protective film is about 0-3 nm.

8. The optical protective film as claimed in claim 1, wherein an $R_{th}$ value of the optical protective film is about 0-100 nm.

9. The optical protective film as claimed in claim 1, wherein haze of the optical protective film is about 0.1-2.0.

10. The optical protective film as claimed in claim 1, wherein thickness of the optical protective film is about 1-500 μm.

* * * * *

UNITED STATES PATENT AND TRADEMARK OFFICE
CERTIFICATE OF CORRECTION

| | | |
|---|---|---|
| PATENT NO. | : 8,455,093 B2 | Page 1 of 1 |
| APPLICATION NO. | : 12/778116 | |
| DATED | : June 4, 2013 | |
| INVENTOR(S) | : Chang et al. | |

It is certified that error appears in the above-identified patent and that said Letters Patent is hereby corrected as shown below:

On the title page, item [75], delete "Chiunn-Wen Chen" and insert --Wen-Jiunn Chen--.

Signed and Sealed this
Eleventh Day of February, 2014

Michelle K. Lee
*Deputy Director of the United States Patent and Trademark Office*